(12) United States Patent
Ono (10) Patent No.: US 7,113,695 B2
(45) Date of Patent: Sep. 26, 2006

(54) HEAT TREATMENT SYSTEM USING SUPERHEATED STEAM

(75) Inventor: Tatsumi Ono, 145 Nakayamacho, Midori-ku, Yokohama-shi, Kanagawa (JP), 226-0011

(73) Assignees: Aoki Kogyo Kabushikikaisha, Chiba (JP); Tatsumi Ono, Kanagawa (JP)

( * ) Notice: Subject to any disclaimer, the term of this patent is extended or adjusted under 35 U.S.C. 154(b) by 261 days.

(21) Appl. No.: 10/922,867

(22) Filed: Aug. 23, 2004

(65) Prior Publication Data
US 2005/0254803 A1 Nov. 17, 2005

(30) Foreign Application Priority Data
May 12, 2004 (JP) .................................. 2004-142096

(51) Int. Cl.
*A61H 33/12* (2006.01)

(52) U.S. Cl. ........................... 392/405; 392/490; 126/20
(58) Field of Classification Search ................ 392/398, 392/405, 441, 449, 490; 126/20
See application file for complete search history.

(56) References Cited
U.S. PATENT DOCUMENTS 4,034,203 A * 7/1977 Cooper .................... 392/398
4,823,767 A * 4/1989 Wust ......................... 126/20
5,390,400 A * 2/1995 Jacob et al. ................ 28/274

FOREIGN PATENT DOCUMENTS

| JP | 2000-63848 | 2/2000 |
| JP | 2001-115167 | 4/2001 |
| JP | 2001-214177 | 8/2001 |
| JP | 2001-279253 | 10/2001 |

* cited by examiner

*Primary Examiner*—Thor S. Campbell
(74) *Attorney, Agent, or Firm*—Wenderoth, Lind & Ponack, L.L.P.

(57) ABSTRACT

The present invention provides a heat treatment system, which includes a treatment chamber having an input port and a discharge port for charging and discharging materials to be treated. A heating system including a plurality of pipe-like heaters positioned one after another in serial arrangement is provided so that the heating temperature is gradually increased for heating the steam or the atomized water introduced from the water feeding system into the heaters by applying voltage on the heaters to turn the steam and the atomized water to superheated steam, and for performing heat treatment on the materials to be treated by injecting the superheated steam into the treatment chamber. A circulating system is provided for sucking the superheated steam and the dry distillation gas in the treatment chamber and for supplying the steam and the gas again into the treatment chamber after deodorizing and filtering, and a control unit is provided for controlling operating conditions such as supply quantity of the steam, duration of treatment, etc.

5 Claims, 7 Drawing Sheets

FIG. 7 ated water from the water feeding system, duration of treatment, etc. and for controlling and maintaining the setting conditions.

HEAT TREATMENT SYSTEM USING SUPERHEATED STEAM

BACKGROUND OF THE INVENTION

The present invention relates to a heat treatment system using superheated steam. In particular, the invention relates to a heat treatment system for producing carbides by carbonizing wooden or bamboo materials and for obtaining pyroligneous acid or bamboo vinegar, and for carrying out heat treatment of combustible waste materials, drying treatment of perishable refuse, for carrying out treatment for cooking of foods, thawing of frozen food, and treatment for sterilizing treatment of various types of products including foodstuffs.

As a heat treatment system using superheated steam known in the past, a system disclosed, for instance, in JPA-2001-115167 is known. This system comprises superheated steam generating means, a sealable type dry distillation oven, a container with free ventilation for accommodating raw materials such as wooden or bamboo materials, a spray nozzle for spraying the superheated steam to the materials in the container, cooling and collecting means for collecting dry-distilled vinegar from the gas, containing thermally decomposed products generated from the dry distillation oven, and a chimney for discharging the gas from inside. In this heat treatment system, the gas generated from wooden or bamboo materials by spraying of the superheated steam is maintained at a predetermined temperature until effective thermal decomposition products are generated while the materials are enclosed in the dry distillation oven, and the cooling and collecting means after confirming the generation of the effective thermal decomposition products.

In the conventional type heat treatment system as described above, only one type of steam superheating unit is provided in the superheated steam generating means. Thus, the temperature of the steam cannot be increased beyond a certain limit. As a result, this system cannot be used for a temperature treatment such as a dry and carbonizing treatment performed in the temperature range of 400–600° C., for an activation treatment in the temperature range of 900–1100° C., or for a graphitization treatment performed in the temperature range of 1500–2300° C. Also, the gas discharged from a chimney contains thermal decomposition products and this gives harmful effects to the environment.

SUMMARY OF THE INVENTION

To solve the above problems, it is an object of the present invention to provide a new type of heat treatment system using superheated steam. To attain the object, the present invention provides a heat treatment system, which comprises a treatment chamber with an input port and a discharge port for charging and discharging the materials to be treated, a water feeding system for feeding steam or atomized water, a heating system for turning the steam or the atomized water introduced from the water feeding system to superheated steam via a plurality of pipe-like heaters positioned one after another in serial arrangement with heating temperature gradually increasing and for discharging the superheated steam into the treatment chamber, a circulating system for sucking the superheated steam and the dry distillation gas in the treatment chamber into a suction and reflux pipe and for supplying the steam and the gas again into the treatment chamber after deodorizing and filtering, and a control unit for setting the operating condition such as the voltage to be applied, supply quantity of steam or

DESCRIPTION OF THE PREFERRED EMBODIMENTS

As shown in FIG. 1 to FIG. 3 and FIG. 6, a heat treatment system 1 comprises a treatment chamber 5, a pair of heating systems 9 and 9 disposed in the treatment chamber 5, a water feeding system 6 connected with the heating systems 9 and 9, a circulating system 12 connected with the treatment chamber 5, and a controller 13 for controlling the whole system.

Figure 1:
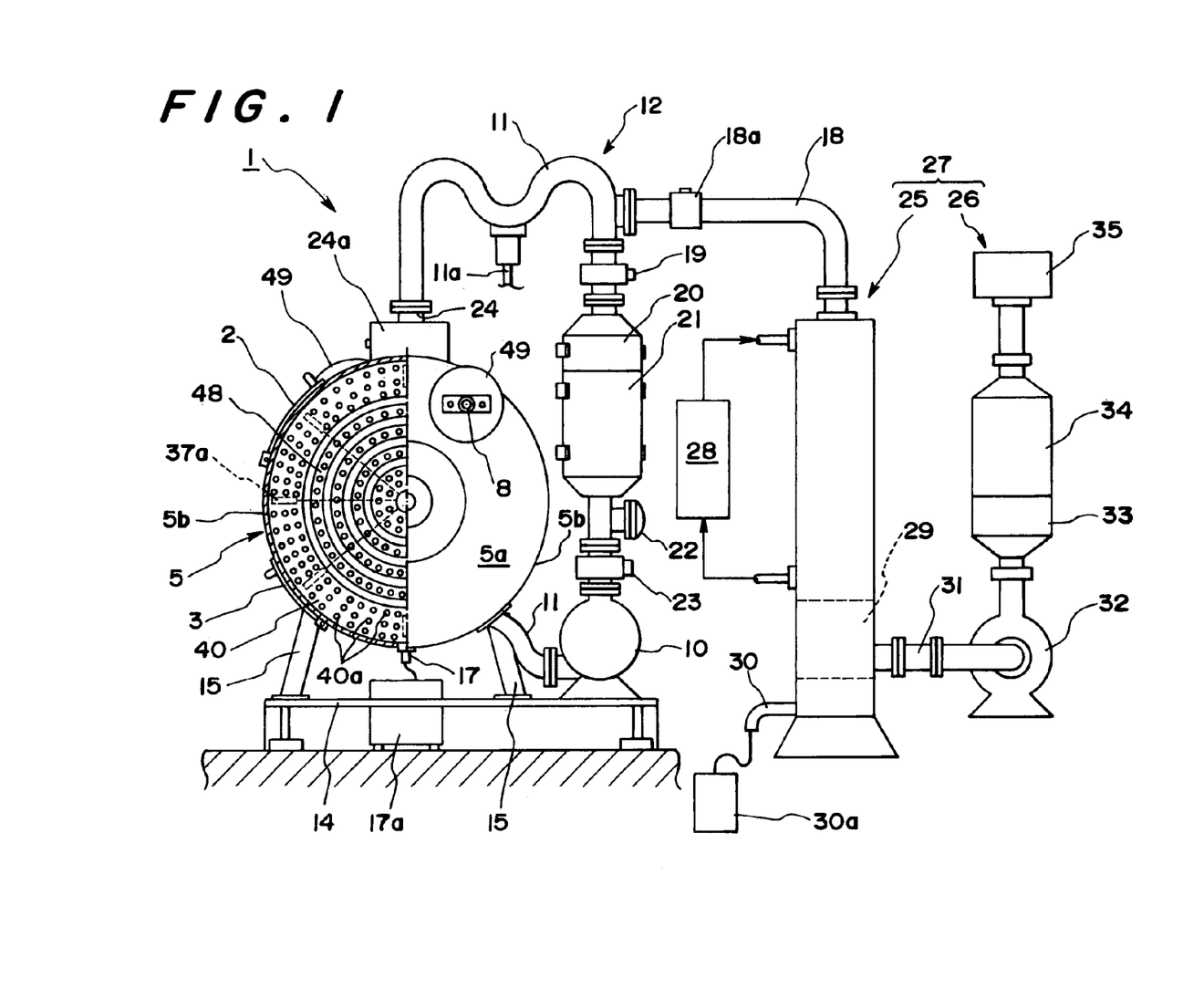
FIG. 1 is a partially cutaway front view showing an internal portion of a heat treatment system.
Figure 2:
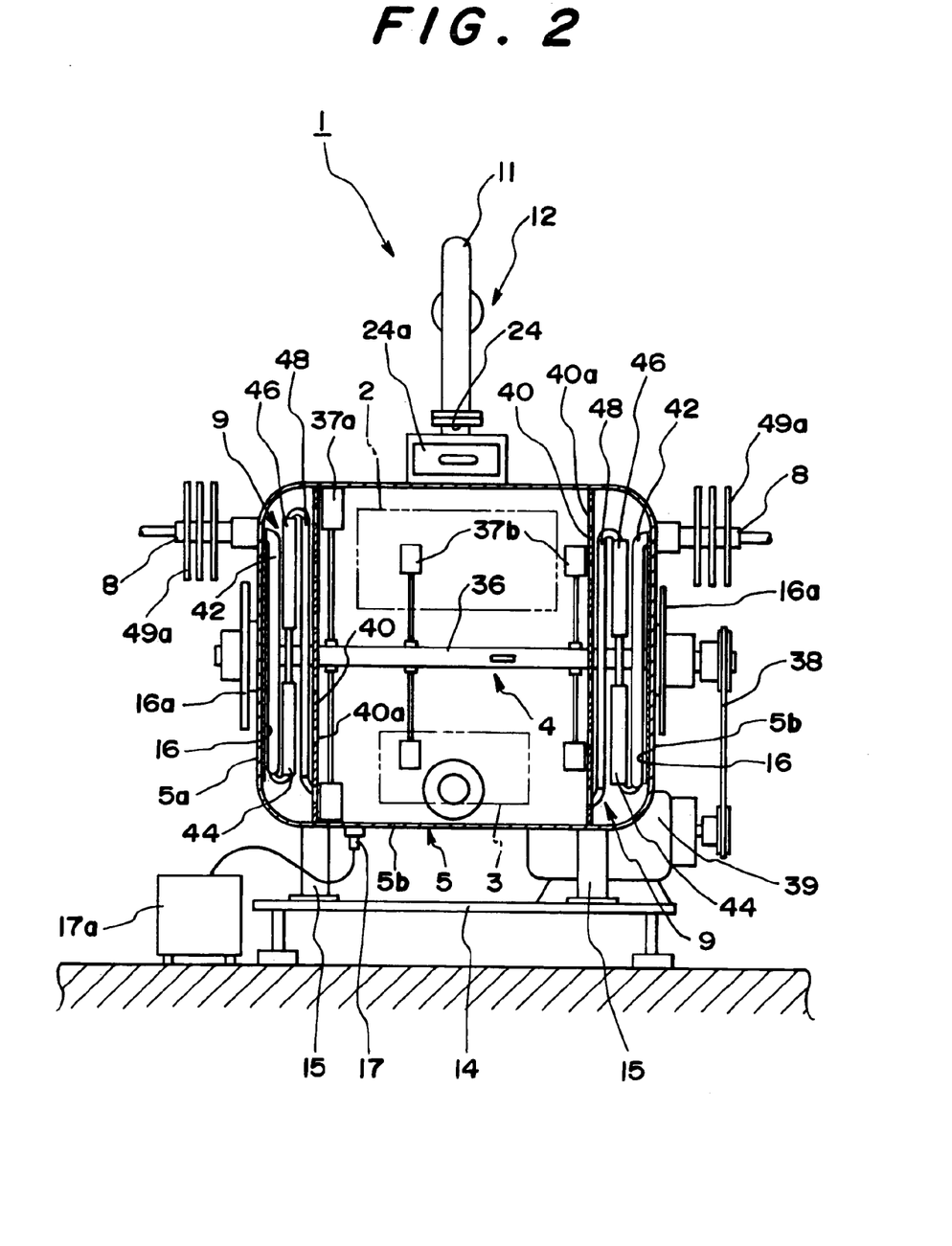
FIG. 2 is a longitudinal sectional side view of the heat treatment system.

The treatment chamber 5 comprises end walls 5a and 5a at each end respectively and a peripheral wall 5b in cylindrical shape, each made of electroconductive materials such as stainless steel. An input port 2 for charging the materials to be treated and a discharge port 3 for taking out and discharging the treated materials are provided on the peripheral wall 5b, and an agitating system 4 is disposed inside.

The pair of heating systems 9 and 9 have the same arrangement and construction. Each system 9 comprises three heaters 42, 44 and 46, each in the form of a pipe (to be described later) and a discharge pipe 48, and these are positioned inside each of the end walls 5a and 5a in the treatment chamber 5. One end of the discharge pipe 48 serves as a discharge outlet 7 positioned inside the treatment chamber 5. One end of the heater 42 at the other end of the discharge pipe penetrates the treatment chamber 5 under an airtight and insulated condition and is opened to outside of the treatment chamber 5 to serve as introducing ports 8 and 8. To these introducing ports 8 and 8, one end of the water supply system 6 is connected. Steam or atomized water supplied by the water feeding system 6 is introduced through the introducing ports 8 and 8. By applying voltage on the heaters 42, 44 and 46, the introduced steam or atomized water is heated, and superheated steam is generated.

The circulating system 12 sucks the superheated steam or dry distillation gas in the treatment chamber 5 into a suction and reflux pipe 11 by using a reflux blower 10. The superheated steam or dry distillation gas thus sucked is deodorized and filtered through migration route within the suction and reflux pipe 11, and the steam and the gas are supplied again into the treatment chamber 5. Further, the controller 3 determines application voltage and supply quantity of steam or atomized water. It also sets up operating conditions such as treatment duration and controls the operation to maintain the setting condition.

As shown in FIG. 1 and FIG. 2, the treatment chamber 5 is supported at horizontal position by four support members 15 on a base 14. The inner side of each of the end walls 5a and 5a is covered with ceramic reflectors 16 and 16 to protect the end walls 5a and 5a from excessive heat and to increase thermal efficiency by reflecting heat rays such as far infrared radiation. Further, the peripheral wall 5b and the end walls 5a and 5a are electrically grounded. Also, at the bottom of the peripheral wall 5b, a drain 17 is provided to discharge liquid such as water or pyroligneous acid, which has been extracted from the treated materials by thermal decomposition and collected in the treatment chamber 5.

A drain tank 17a is connected to the drain 17, and liquid such as water, pyroligneous acid, etc. discharged through the drain 17 is accumulated for once. A heat radiation plate 16a is arranged on a rotation shaft 36 of the agitating system 4 at a position closer to outer surfaces of the end walls 5a and 5a, and this prevents overheating of the rotation shaft 36 and the troubles of rotation on bearing portion.

As shown in FIG. 1, the circulating system 12 comprises a drain 11a, a branching pipe 18 with a changeover valve 18a, a first stop valve 19 for interrupting the migration channel as necessary, a temperature regulating heater 20, a deodorizer-filter 21 for deodorizing and filtering, a regulator valve 22 for regulating flow rate of superheated steam and dry distillation gas, and a second stop valve 23—arranged in this order from upstream side to downstream side in the migration channel of the superheated steam or dry distillation gas flowing in the suction and reflux pipe 11.

The drain 11a is used to prevent troubles in the functions of the temperature regulating heater 20 or the deodorizer-filter 21 when the steam or the dry distillation gas are liquefied due to rapid temperature decrease caused by external air, and the liquefied substance flows into the temperature regulating heater 20 or the deodorizer-filter 21. The drain 11a is connected with a drain tank (not shown).

The temperature regulating heater 20 is used to maintain adequate temperature so that the function of the deodorizer-filter 21 is not deteriorated. The regulating valve 22 is used to regulate internal pressure by opening automatically when the pressure inside the treatment chamber 5 is increased due to thermal expansion of the superheated steam and the dry distillation gas.

Further, one end of the suction and reflux pipe 11 penetrates airtightly through a lower portion of the peripheral wall 5b of the treatment chamber and is opened to the interior of the treatment chamber 5. The other end of the suction and reflux pipe 11 airtightly passes through an upper portion of the peripheral wall 5, serving as a suction port 24, and is opened to the interior of the treatment chamber 5. At a portion upstream of the suction port 24, a filter 24a of known type is provided.

The circulating system 12 sucks the superheated steam and the dry distillation gas from the suction port 24 by the sucking action of the reflux blower 10 and filters the steam and the gas through the filter 24a. Then, the steam and the gas are deodorized and filtered by the deodorizer-filter 21 and are supplied again into the treatment chamber 5.

As shown in FIG. 1, an auxiliary treatment system 27 is connected to the branching pipe 18. The auxiliary treatment system 27 comprises a cooling unit 25 for cooling the superheated steam or the dry distillation gas and a gas treatment unit 26. The gas treatment unit 26 is used to regulate temperature of the superheated steam or the dry distillation gas cooled by the cooling unit 25 and to discharge the dry distillation gas to external air after the deodorizing process. The cooling unit 25 comprises, in an upper portion, a cooling tower 28 for circulating and cooling the superheated steam or the dry distillation gas, a filter 29 for filtering a liquefied moisture component, and a drain 30 for collecting the filtered water. The drain 30 is connected to a drain tank 30a. The gas treatment unit 26 is connected to a lower portion of the cooling unit 25 via a connection pipe 31, and it comprises a suction blower 32 connected to the connection pipe 31, a deodorizer 34, a temperature regulating heater 33 for regulating temperature of the dry distillation gas sent from the suction blower 32 to adequately maintain the function of the deodorizer 34, and an exhaust hood 35.

The auxiliary treatment system 27 is operated when necessary, e.g. in case the heat treatment operation has been completed, or in case the quantity of the superheated steam or the dry distillation gas in the treatment chamber should be reduced during heat treatment operation. The first stop valve 19 and the second stop valve 23 are switched over from an open condition to a closed condition, and the changeover valve 18a of the branching pipe 18 is switched over from a closed condition to an open condition, and the flow of the superheated steam and the dry distillation gas in the suction and reflux pipe 11 is guided into the branching pipe 18.

As shown in FIG. 2, the agitating system 4 provided inside the treatment chamber 5 has a rotation shaft 36 with both ends pivotally and airtightly supported on the end walls 5a and 5a and the shaft extends in the horizontal direction to outside of the treatment chamber 5. On the rotation shaft 36, there are provided a long size agitating vane 37a rotating along a circumference near the inner surface of the peripheral wall 5b and 2 sets of short size agitating vanes 37b and 37b rotating along a circumference with a smaller diameter than that of the above circumference. An endless belt 38 is stretched over a sprocket provided on one outer end of the rotation shaft 36 and a sprocket provided on a driving shaft of a driving motor 39 mounted on the base 14. The rotating force of the driving motor 39 is transmitted to the rotation shaft 36 via the endless belt 38. This prevents the transmission of the high temperature of the rotation shaft 36 directly to the driving motor 39, and the decrease of the function of the driving motor 39 can be avoided.

Also, a pair of partition walls 40 and 40 are provided, and this makes it possible to prevent the pair of heating systems 9 and 9 from being brought into contact with the treated materials. On the partition walls 40 and 40, there are provided a number of holes 40a, through which the superheated steam discharged from discharge outlets 7 and 7 of the heating systems 9 and 9 passes. The agitating system 4 is in heat treatment operation mode at high-speed rotation during heat treatment. When heat treatment has been completed and the treated materials have been taken out, it is switched over to the takeoff operation mode at low-speed rotation, and the treated materials are taken out of the discharge port 3.

Figure 3:
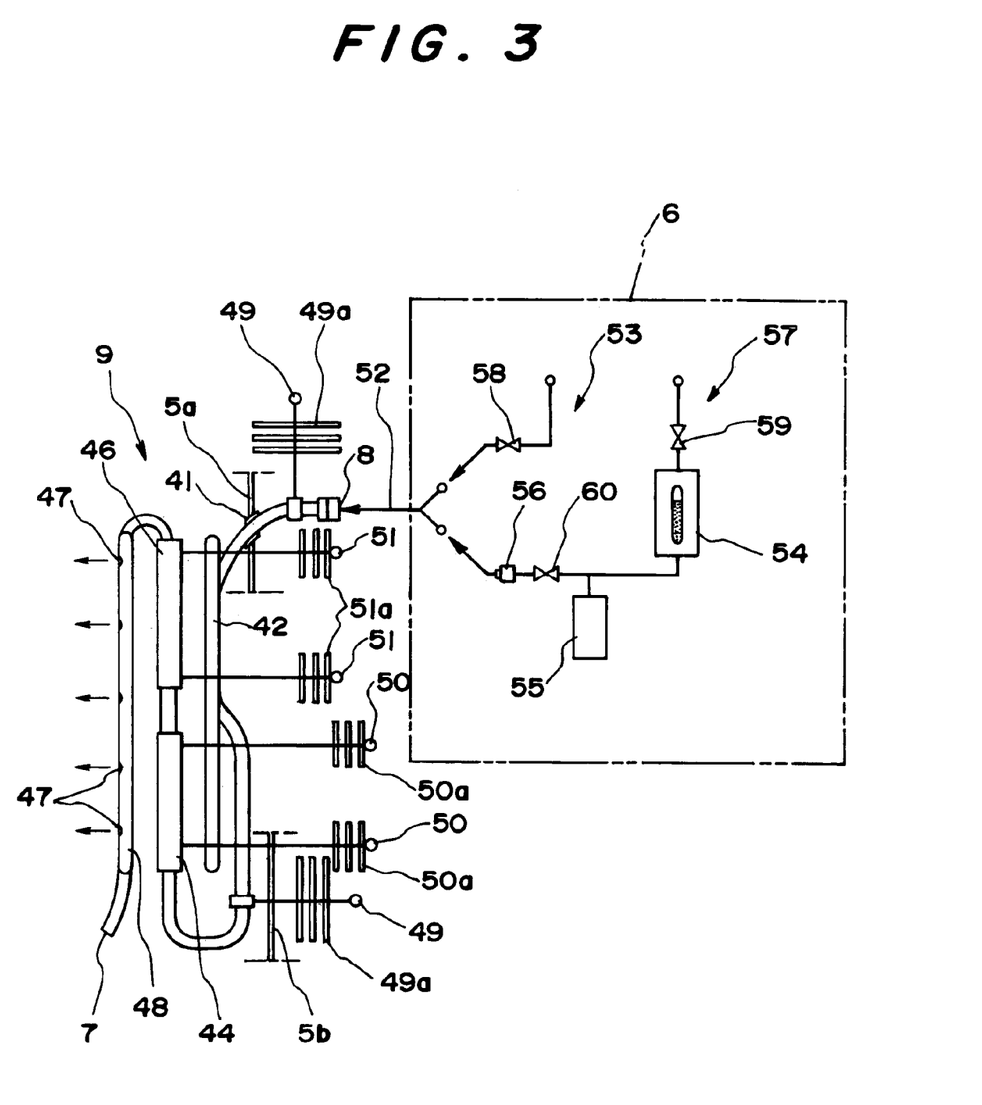
FIG. 3 is a side view of a heating system showing a connecting condition with a water feeding system.
Figure 4:
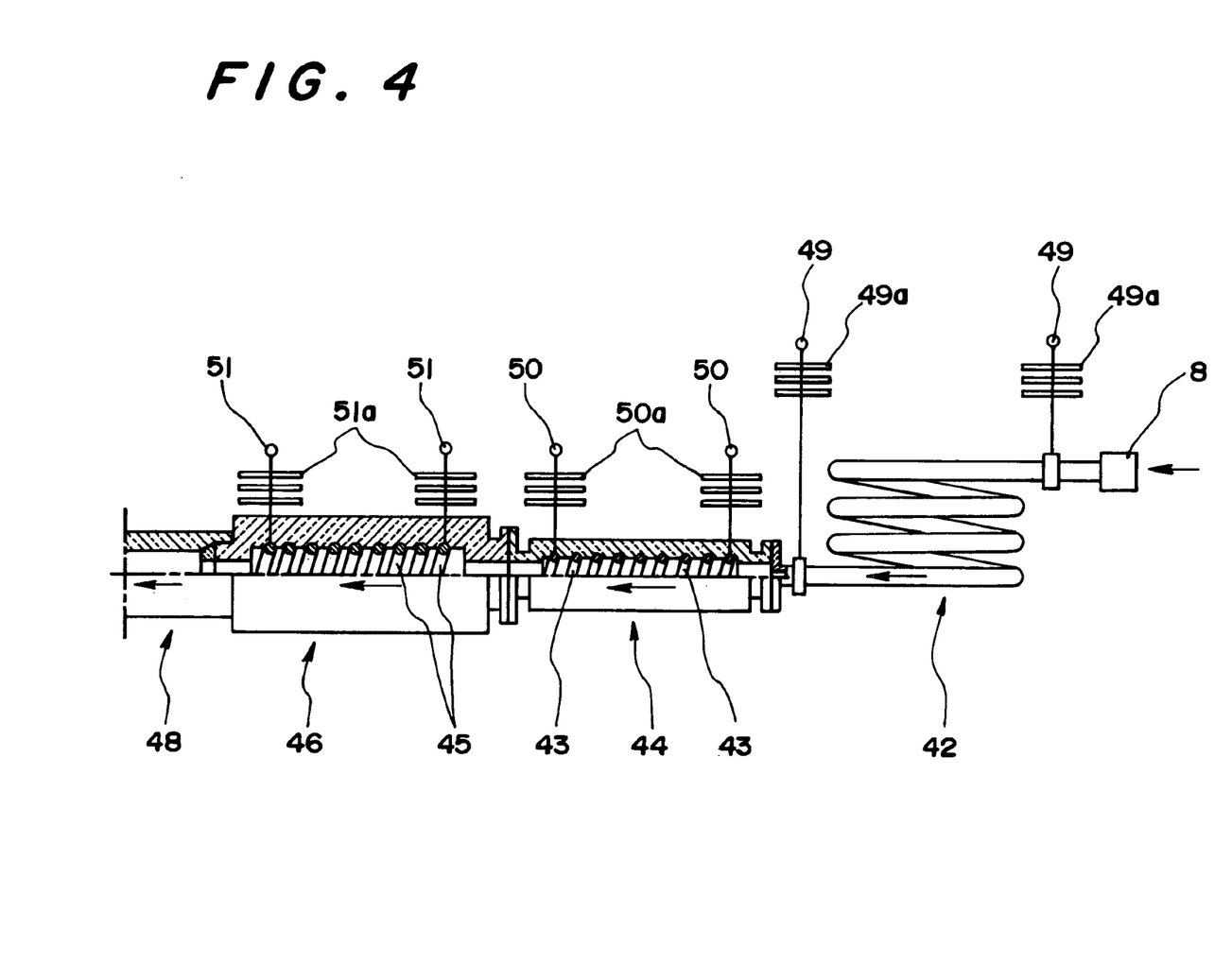
FIG. 4 is a schematical drawing of an essential portion of a heating system.
Figure 5:
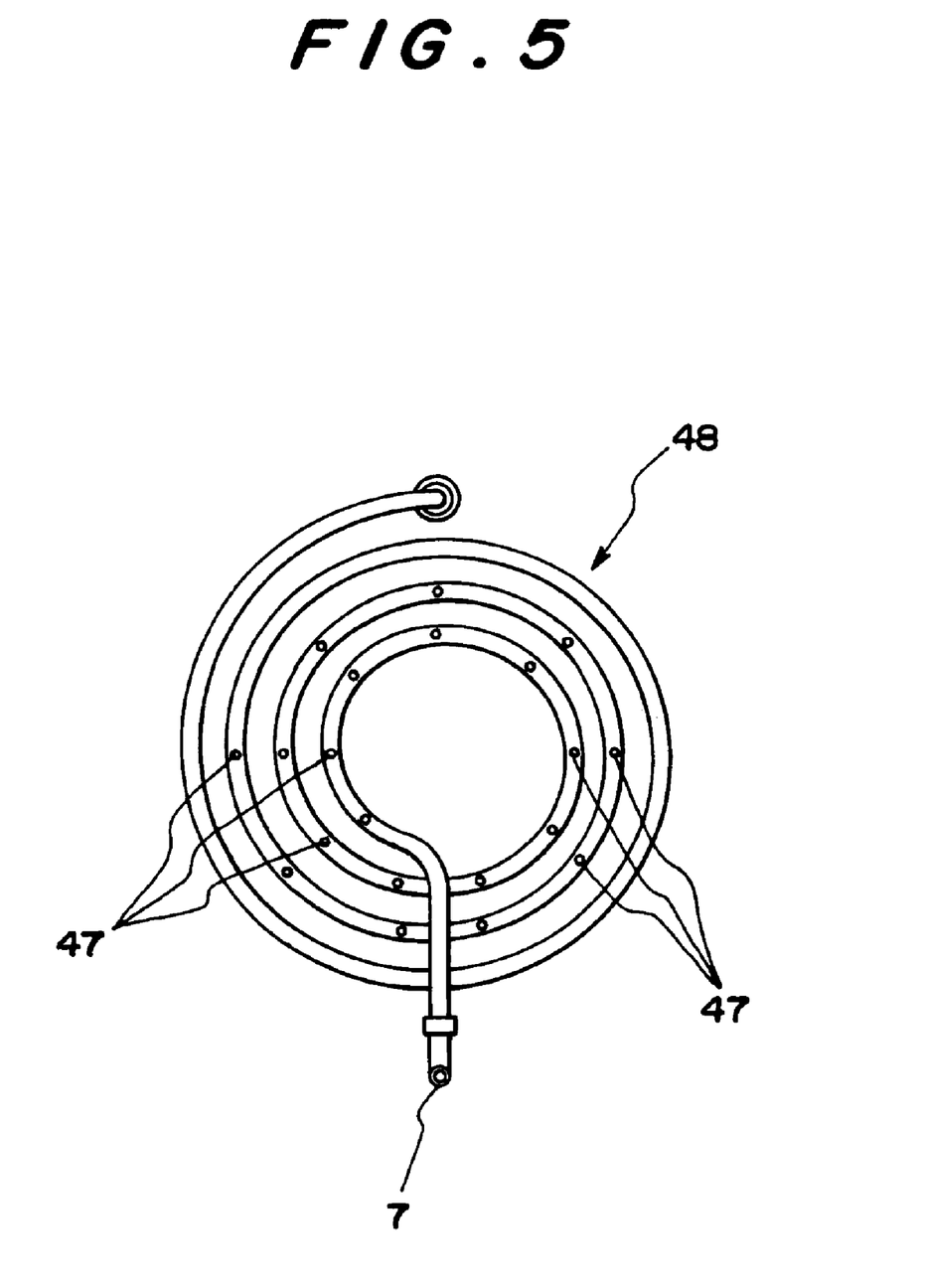
FIG. 5 is an enlarged front view of a discharge pipe.

Next, a detailed description will be given of the pair of heating systems 9 and 9. Each of the heating systems has the same arrangement and construction, and description is given here only of a heating system 9. As shown in FIG. 3–FIG. 5, the heating system 9 comprises a pipe heater 42, serving as a high temperature preheater for heating in a range of 100–600° C., a silicon carbide module heater 44, serving as a high temperature heater of pipe-like shape for heating in a range of 600–1400° C., a graphite module heater 46, serving as a super-high temperature heater of pipe-like shape for heating in a range of 1400–2800° C., and a discharge pipe 48.

In the pipe heater 42, a pipe made of electroconductive material such as inconel, Hastelloy, or stainless steel is arranged in spiral form along the inner side of the end wall 5a, and it airtightly penetrates through the end wall 5a via an electric insulating material 41 (FIG. 3). As is evident from FIG. 4, the silicon carbide module heater 44 is a pipe-like heater made of a non-metal material with a silicon carbide coil 43 incorporated in it. The graphite module heater 46 is a pipe-like heater made of a non-metal material and with a graphite coil 45 incorporated in it.

A discharge pipe 48 is made of a non-metal material and is connected to the graphite module heater 46, and the discharge pipe has a number of discharge holes 47 on its peripheral surface, and its forward end is formed as the discharge outlet 7. A metal pipe is used to connect the heater 42 with the heater 44. The heater 44 is connected with the heater 46 via a pipe made of a non-metal material. The non-metal material pipe is used for connecting the silicon carbide module heater 44, the graphite module heater 46, the discharge pipe 48 and the heaters 44 and 46. This is because the pipe may be destroyed by heat of about 1000° C. if it is made of a metal material.

As shown in FIG. 4, a pair of the first power terminals 49 and 49 mounted with heat radiation plates 49a and 49a are provided on the introducing port 8 and on outlet side of the pipe heater 42. On both ends of the silicon carbide coil 43 of the silicon carbide module heater 44, a pair of second power terminals 50 and 50 with heat radiation plates 50a and 50a are disposed. On both ends of the graphite coil 45 of the graphite module heater 46, a pair of third power terminals 51 and 51 with heat radiation plates 51a and 51a are provided. By applying a predetermined voltage on each pair of the first, the second and the third power terminals 49, 49, 50, 50, 51 and 51 respectively, the steam in the heaters 42, 44 and 46 is heated.

As shown in FIG. 3, a supply pipe 52 of the water feeding system 6 for supplying steam or atomized water is connected to the introducing port 8 of the pipe heater 42. The water feeding system 6 comprises a first feeding unit 53 and a second feeding unit 57. The first feeding unit 53 is used to supply the steam, and it is connected to a boiler (not shown). The second feeding unit 57 is to feed water, and it comprises a tank 54 for storing water and connected to city waterworks, a pressure pump 55 for applying pressure on the water supplied from the tank 54, and a spray nozzle 56 for spraying water in atomized state. In the second feeding unit 57, warm water may be supplied instead of water.

In FIG. 3, reference numeral 58 denotes a control valve for regulating flow rate at the first feeding unit 53, the numeral 59 denotes a control valve for regulating flow rate of water to the tank 54 of the second feeding unit 57, and the numeral 60 represents a control valve for regulating flow rate of water to the spray nozzle 56 of the second feeding unit 57.

The heating system 9 introduces the steam or the atomized water through the introducing port 8 from the water feeding system 6. By applying a predetermined voltage on each of the pairs of the first, the second, and the third power terminals 49, 49, 50, 50, 51 and 51 respectively via a power transformer 61 (FIG. 6) from commercial power source, the pipe heater 42, the silicon carbide module heater 44, and the graphite module heater 46 are operated. The steam or the atomized water in the heaters is turned to superheated state, and the superheated steam is generated. As described above, temperature of the steam heated in the pipe heater 42 is in the range of 100–600° C. In the silicon carbide module heater 44, the steam heated in the pipe heater 42 is heated further, and steam temperature is increased to the range of 600–1400° C. In the graphite module heater 46, the steam heated in the silicon carbide module heater 44 is heated further, and steam temperature is increased to the range of 1400–2800° C. In the heating system 9, it is possible to control the operation of each of the heaters 42, 44 and 46 according to the type of heat treatment and to change the temperature of the superheated steam.

Figure 6:
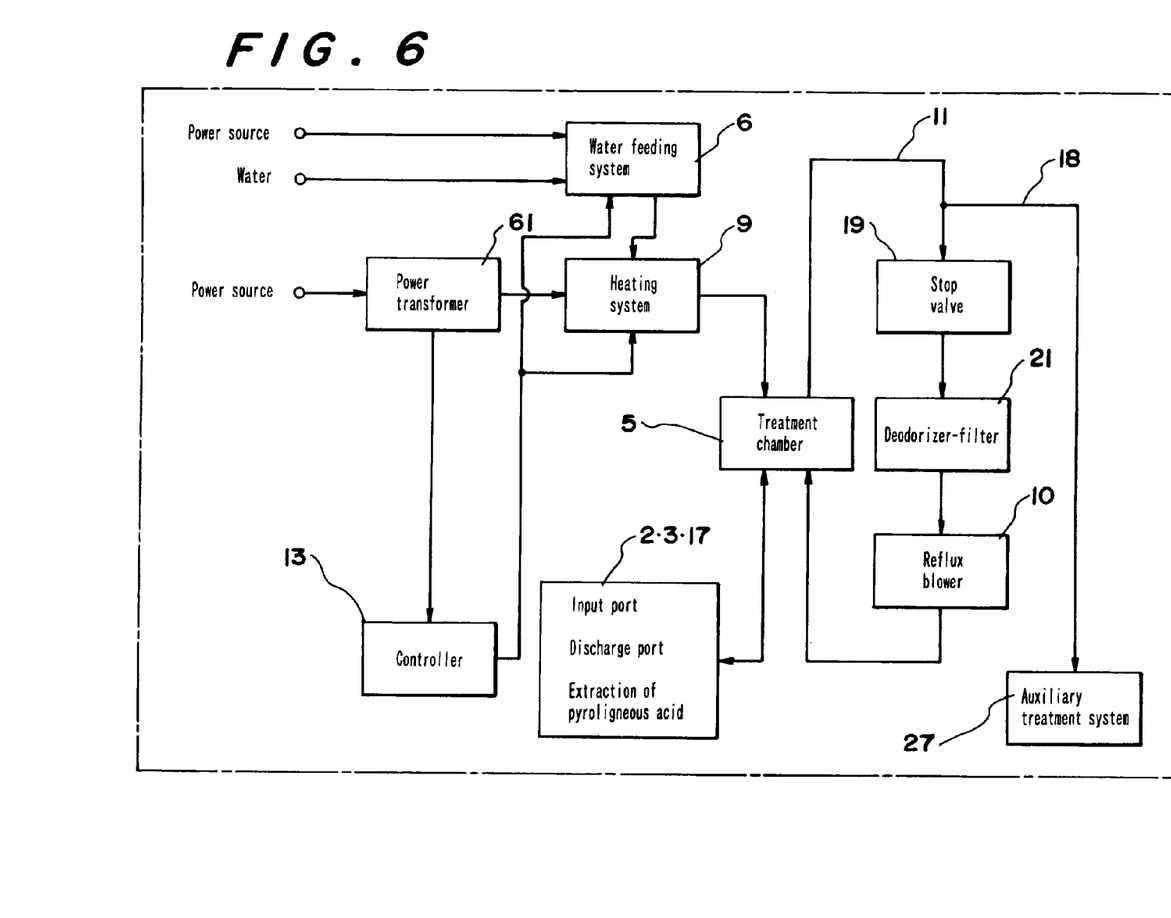
FIG. 6 is a block diagram showing the entire arrangement of the heat treatment system.
Figure 7:
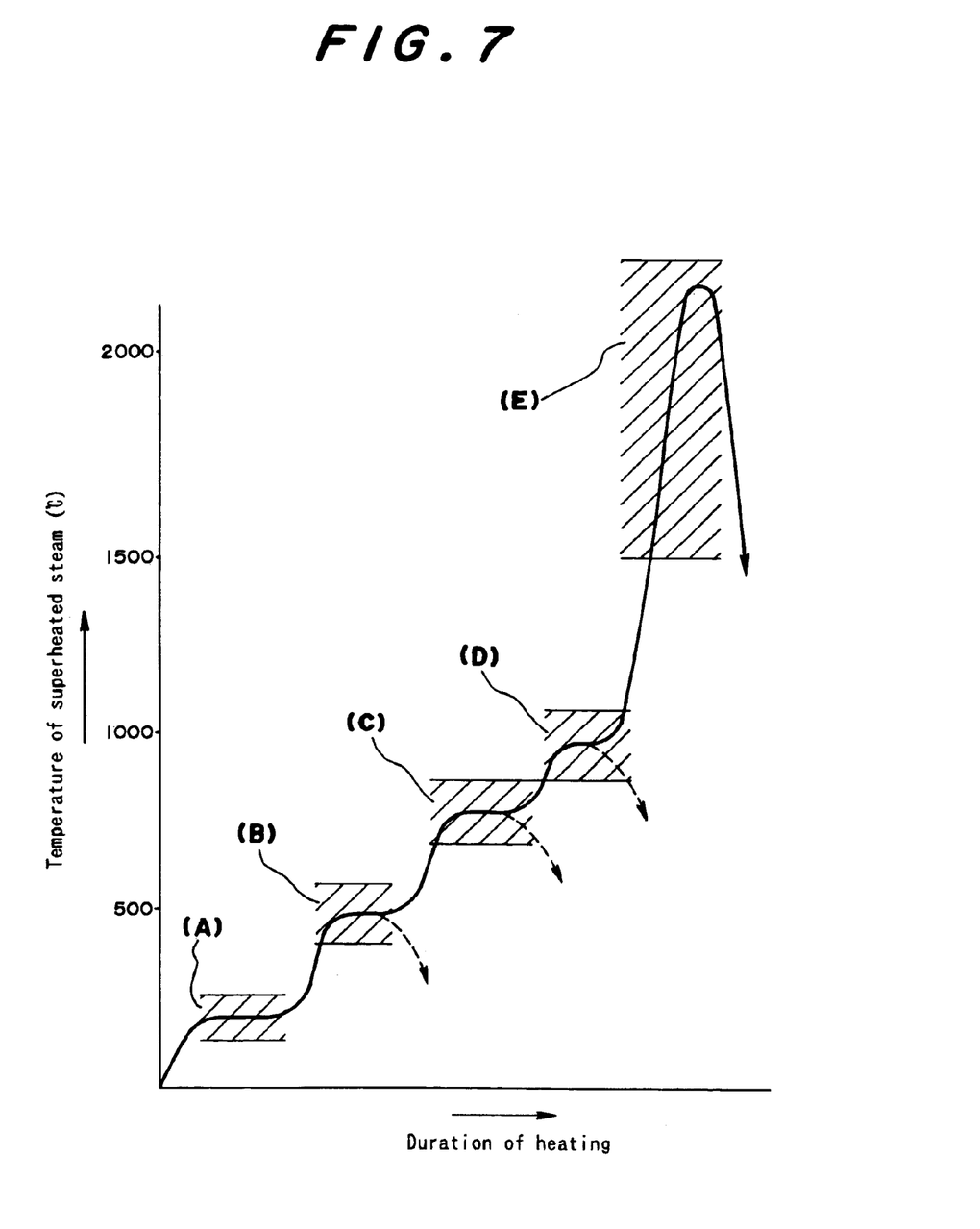
FIG. 7 is a graph showing a relation between duration of heating and temperature change in the heat treatment process.

As shown in FIG. 6, the controller 13, acting as a control unit, comprises an IC circuit of known type (not shown), which controls voltage to be applied on each of the first, the second and the third power terminals 49, 50, and 51 (control of the power transformer 61), controls quantity of steam to be supplied to the pipe heater 42 (control of the control valves 58, 59 and 60 of the water feeding system 6), and controls key or volume control of known type (not shown), acting as input means for setting the operating condition such as treatment duration and for controlling the preset working condition. By setting the input to the controller 13, it is possible to operate with the temperature at the discharge of the superheated steam in the range of 100–2800° C.

In the heat treatment system 1 as described above, by setting the temperature and the heating duration by the controller 13 adequate for each type of the materials to be treated, it is possible to carry out extraction treatment (A), dry carbonizing treatment (B), carbonizing treatment (C), activation treatment (D), and graphitization treatment (E). Also, it is possible to continuously carry out necessary treatment sequentially by automatic operation of each of the treatments (A)–(E) to the same material to be treated.

The extraction treatment (A) is to extract water and solvent (such as pyroligneous acid) from the materials to be treated through thermal decomposition. The extraction treatment (A) can be preferably used, for the first place, in the treatment of waste or refuse of vegetables, fruits, fishes, rejected products and other foodstuffs brought on in food processing factories, vegetable markets, fish markets, etc. Secondly, it can be used in roasting and boiling treatment for coffee, Japanese tea, oolong tea, medicinal herb, etc. and in moisture removing treatment at the manufacturers of drinks. Thirdly, it is preferably used in the volume reducing treatment for packaging materials, bags and pouches, tray and containers, etc. Fourthly, it is used in the extraction treatment of bamboo vinegar, wood vinegar, etc. produced from bamboo, wood, (e.g. chips of thinning lumber). Input conditions of the controller 13 in the extraction treatment (A) are determined according to the quantity or the types of the materials to be treated. Preset temperature is in the range of about 150–250° C., and the preset heating time is in the range of about 30–60 minutes.

In the extraction of bamboo vinegar, wood vinegar, or medicinal solution, 80–90% of moisture or contained solvents of the materials to be treated is processed by radiation heat transfer or condensation heat transfer specific to the superheated steam by thermal decomposition of composite thermal energy. The extracted liquid is guided from the drain 17 to the drain tank 17a and is accumulated there. After the processing in the treatment of waste and refuse, the agitating system 4 is switched over to the takeoff operation mode at low speed rotation, and the solidified materials are taken out of the discharge port 3.

In the extraction treatment (A), the pipe heater 42, the silicon carbide module heater 44, and the graphite module heater 46 in the heating systems 9 and 9 are operated until the preset temperature is reached. After the preset temperature has been reached, the operation of the silicon carbide module heater 44 and the graphite module heater 46 are stopped, and heating is carried out only by the pipe heater 42.

The drying and carbonizing treatment (B) is performed after the extraction treatment (A), and it comprises two steps: a drying step and a carbonizing step. In the first step, i.e. in drying step, the preset temperature is set to the range of 400–600° C. depending on the type of the material to be treated, and drying is carried out for a certain period of time until the material is dried to have moisture content as desired. By performing heat treatment for the extended period of time, almost all of the organic substances such as hemi-cellulose, cellulose, lignin, etc. are decomposed by thermal decomposition, and it is turned to the second step, i.e. carbonizing process. After the treatment, the agitating system 4 is switched over to the takeoff operation mode at low speed rotation, and the carbides are taken out of the discharge port 3.

Similarly to the case of the extraction treatment (A), in the drying and carbonizing treatment (B), the pipe heater 42, the silicon carbide module heater 44, and the graphite module heater 46 are operated in the heating systems 9 and 9 until the preset temperature is reached. After the preset temperature has been reached, operations of the silicon carbide module heater 44 and the graphite module heater 46 are stopped, and the material to be treated is heated only by the pipe heater 42.

The carbonizing treatment (C) is carried out after the extraction treatment (A) and the drying and carbonizing treatment (B). The temperature is set to the range of 700–900° C., and the treatment is performed for the time period as required. The duration of the treatment may be shorter because of the effects of radiation heat transfer and condensation heat transfer specific to the superheated steam. Because the treatment temperature is high, carbide with better quality and with higher carbon content than the carbide obtained in the drying and carbonizing treatment (B) can be attained. After the treatment, the agitating system 4 is switched over to the takeoff operation mode at low speed rotation, and the carbide with better quality and higher carbon content is taken out of the discharge port 3.

In the carbonizing treatment (C), the pipe heater 42, the silicon carbide module heater 44, and the graphite module heater 46 in the heating systems 9 and 9 are operated until the preset temperature is reached. After the preset temperature has been reached, the operation of the graphite module heater 46 is stopped, and heating is performed only by the pipe heater 42 and the silicon carbide module heater 44.

The activation treatment (D) is carried out after the extraction treatment (A), the drying and carbonizing treatment (B), and the carbonizing treatment (C). The temperature is set to the range of 900–1100° C. and the treatment is carried out for the time period as required, and activated carbon is obtained. In this activation treatment (D), particles of the superheated steam gasified by the effects of radiation heat transfer and condensation heat transfer specific to the superheated steam enter from the surface of the carbide by forming routes of complicated shape. Then, on the walls with macro-holes and meso-holes formed in the carbonizing treatment (C), a large number of micro-holes are formed through the intrusion routes. As a result, activated carbon with a larger specific surface area and larger pore volume and with higher absorbability can be obtained. After the treatment, the agitating system 4 is switched over to the takeoff operation mode at low speed rotation, and the activated carbon is taken out of the discharge port 3.

In this activation treatment (D), similarly to the case of the carbonizing treatment (C), the pipe heater 42, the silicon carbide module heater 44, and the graphite module heater 46 in the heating systems 9 and 9 are operated. After the preset temperature has been reached, the operation of the graphite module heater 46 is stopped, and heating is performed only by the pipe heater 42 and the silicon carbide module heater 44.

The graphitization treatment (E) is carried out after the extraction treatment (A), the drying and carbonizing treatment (B), the carbonizing treatment (C) and the activation treatment (D). The temperature is set to the range of 1500–2300° C., and the treatment is performed for the time period as required. Graphite of good quality with higher carbon content and with graphite structure of carbon atoms in the most stabilized state can be obtained. In the graphitization treatment (E), voltage is applied on all of the pipe heater 42, the silicon carbide module heater 44, and the graphite module heater 46 of the heating systems 9 and 9.

In the graphitization treatment (E), the pipe heater 42, the silicon carbide module heater 44, and the graphite module heater 46 of the heating systems 9 and 9 are operated until the preset temperature is reached. After the preset temperature has been reached, temperature is controlled by stopping or restarting the operation of the graphite module heater 46.

Next, a description will be given of the operation of the heat treatment system 1 as described above. Operating conditions are inputted to the controller 13 depending on the types of the materials to be treated and the type of treatment. By controlling the power transformer 61, a predetermined voltage is applied to each of the first, the second, and the third power terminals 49, 50, and 51 respectively. Then, depending on the preset temperature, a predetermined voltage is applied only to the first and the second power terminals 49 and 50, or a predetermined voltage is applied only on the first power terminal 49, and the heating systems 9 and 9 are operated and controlled. At the same time, the water feeding system 6 is controlled and a predetermined quantity of the steam or the atomized water is supplied to the heating systems 9 and 9. Then, the driving motor 39 is started and the agitating system 4 is turned to heat treatment operation mode. The long size agitating vane 37a and the short size agitating vanes 37b and 37b are rotated at high speed, and the materials to be treated in the treatment chamber 5 are agitated.

The steam or the atomized water supplied to heating systems 9 and 9 is heated stepwise by the pipe heater 42, the silicon carbide module heater 44, and the graphite module heater 46, and it is turned to superheated steam. It is discharged through the discharge outlets 7 and 7 and the discharge hole 47, and after passing through the holes 40a on the partition walls 40 and 40, it enters the treatment chamber, and heat treatment is performed on the material to be treated.

The dry distillation gas generated from the superheated steam and the materials to be treated in the treatment chamber 5 is sucked into the suction and reflux pipe 11 from the suction port 24 via the filter 24a under the sucking action of the reflux blower 10 of the circulating system 12. It further passes through the temperature regulating heater 20 and is deodorized and filtered by the deodorizer-filter 21 and is then supplied again to the treatment chamber 5. As described above, the heat treatment system 1 can achieve energy saving on the heat source and can accomplish heat treatment with high efficiency. The gas with hideous odor from the materials being treated is thermally decomposed in the treatment chamber 5. It is filtered when passing through the filter 24a and is further filtered by the deodorizer-filter 21. It is then sent back to the treatment chamber 5 and is thermally decomposed. By repeating this procedure, odor and impurities are removed in reliable manner. During this heat treatment, oxygen deficiency condition occurs in the treatment chamber 5 due to the characteristics of the superheated steam. Thus, the perishable refuse or the generated dry distillation gas does not burn, and harmful substances such as dioxin caused from burning are not generated.

When it is wanted to decrease the quantity of the superheated steam or the dry distillation gas in the treatment chamber 5 during heat treatment operation or after the completion of heat treatment, the auxiliary treatment system 27 is operated. Specifically, the stop valves 19 and 23 are switched over from an open condition to a closed condition, and the changeover valve 18a is switched over from the closed condition to the open condition. Then, the suction blower 32 is operated, and the superheated steam or the dry distillation gas is introduced into the branching pipe 18 via the suction and reflux pipe 11. The superheated steam or the dry distillation gas is cooled down in the cooling tower 28. The liquefied moisture or component solvents are filtered through the filter 29, and these are collected in the drain tank 30a through the drain 30. The dry distillation gas not liquefied is deodorized by the deodorizer 34 and is discharged to outside through the exhaust hood 35.

After the completion of the heat treatment, the treated materials are discharged from the discharge port 3, and the extraction liquid is taken out from the drain tank 17a.

The present invention is not limited to the above embodiments. For instance, the agitating system 4 may comprise a screw mounted on the rotation shaft instead of the long size agitating vane 37a and the short size agitating vanes 37b and 37b. Also, heat treatment can be accomplished without the agitating system 4 although the duration of treatment may be longer. Further, an automatic charging system (not shown) for charging the materials to be treated into the input port 2 may be provided, or an automatic discharge system (not shown) for discharging the treated materials after the treatment through the discharge port 3 may be used so that automatic operation can be achieved at nighttime on low-cost operation at low power rate at night.

According to the present invention, the superheated steam, i.e. clean heat energy not dependent on combustion, is used as the heat source. Thus, without giving harmful effects on environment, heat treatment can be carried out within a short time. The superheated steam and the dry distillation gas in the treatment chamber 5 are sucked by the reflux blower 10 in the circulating system 12, and after deodorizing and filtering the steam and the gas along the migration route, these are supplied again to the treatment chamber 5. As a result, there is less variation in the temperature within the treatment chamber 5, and temperature control can be carried out in an easy and reliable manner. Further, it is possible to keep the superheated steam and the dry distillation gas in a clean condition. Also, the operating condition can be set and controlled by the controller 13, and this makes it possible to carry out various types of heat treatment automatically and in a reliable manner. The heating systems 9 and 9 comprise a pipe-like high temperature preheater 42, a pipe-like high temperature heater 44, and a pipe-like super-high temperature heater 46 placed in serial arrangement. Thus, a wide temperature range can be set, and different types of heat treatment can be carried out, and not much time is required until the materials are heated at the preset temperature.

Also, by providing the auxiliary treatment system 27, the superheated steam and the dry distillation gas can be introduced to the auxiliary treatment system 27 via the branching pipe 18. The superheated steam is cooled down by the cooling unit 25, and water can be separated from the superheated steam, or the contained solvents can be separated from the dry distillation gas. The dry distillation gas can be deodorized by the gas treatment unit 26 and can be discharged to outside. This provides the effect to attain clean discharge.

What is claimed is:

1. A heat treatment system using superheated steam, comprising:

a treatment chamber with an input port for receiving materials to be treated and a discharge port for discharging materials to be treated;

a water feeding system for supplying steam or atomized water;

heating systems for turning the steam or the atomized water introduced from the water feeding system to superheated steam by a plurality of pipe-like heaters disposed in serial arrangement and with temperature gradually increasing and for discharging the superheated steam into the treatment chamber;

a circulating system for sucking the superheated steam and the dry distillation gas in the treatment chamber into a suction and reflux pipe by a reflux blower, and for supplying the steam and the gas again to the treatment chamber after deodorizing and filtering the steam; and a control unit for setting voltage to be applied, and supply quantity of the steam or the atomized water from the water feeding system, for setting and maintaining operating condition such as duration of treatment, and for controlling and maintaining the preset condition.

2. A heat treatment system using superheated steam according to claim 1, wherein said heating system comprises a pipe-like high temperature preheater, a pipe-like high temperature heater, a pipe-like super-high temperature heater, and a discharge pipe connected one after another, said pipe-like high temperature preheater being connected with a feeding pipe of the water feeding system at an introducing port provided at one end and used for generating the superheated steam by heating steam or atomized water introduced through the introducing port by applying voltage, said pipe-like high temperature heater being operable to turn the superheated steam generated at the high temperature preheater to a steam of higher temperature by applying voltage, said super-high temperature heater being operable to turn the superheated steam heated at the high temperature heater to a steam of still higher temperature by applying voltage, and said discharge pipe being operable to discharge the superheated steam generated at the super-high temperature heater into the treatment chamber.

3. A heat treatment system using superheated steam according to claim 1, further comprising an agitating system for agitating the materials to be treated as the materials are charged into the agitating system.

4. A heat treatment system using superheated steam according to claim 1, further comprising an auxiliary treatment system comprising a changeover valve, said changeover valve being connected to an end of a branching pipe branched from middle portion of the suction and reflux pipe and operable to switch over the flow of superheated steam and dry distillation gas in the suction and reflux pipe to the branching pipe side, said auxiliary treatment system being operable to introduce the superheated steam and the dry distillation gas in the suction and reflux pipe via said branching pipe when necessary, to cool down the superheated steam and the dry distillation gas and separate water from the superheated steam and separate the contained solvents from the dry distillation gas, and to deodorize and discharge the dry distillation gas to outside of the system.

5. A heat treatment system comprising a treatment chamber provided with an input port and a discharge port and with an agitating system for agitating materials charged therein;

a water feeding system for feeding steam or atomized water;

a heating system with a plurality of pipe-like heaters arranged in the treatment chamber, with a first end thereof opened to the treatment chamber to discharge the superheated steam, a second end thereof penetrating through the treatment chamber in an airtight and insulated manner and opened to outside, thereby acting as an introducing port for introducing the steam or the atomized water from said water feeding system and for charging the steam or the atomized water introduced through the introducing port by applying voltage and by heating the steam to turn the steam to the superheated steam and to discharge the steam into the treatment chamber;

a circulating system for sucking the superheated steam and the dry distillation gas in the treatment chamber into the suction and reflux pipe by using a reflux blower, and for supplying the superheated steam and the dry distillation gas into the treatment chamber after deodorizing and filtering the steam and the gas along the migration route when the steam and the gas are moving within the suction and reflux pipe;

an auxiliary treatment system comprising a changeover valve, said changeover valve being connected to an end of a branching pipe branched from a middle portion of the suction and reflux pipe and operable to switch over the flow of superheated steam and dry distillation gas in the suction and reflux pipe to the branching pipe side, said auxiliary treatment system being operable to introduce the superheated steam and the dry distillation gas in the suction and reflux pipe via said branching pipe when necessary, to cool down the superheated steam and the dry distillation gas and separate water from the superheated steam and separate the contained solvents from the dry distillation gas, and to deodorize and discharge the dry distillation gas to outside of the system; and a control unit for setting voltage to be applied, and supply quantity of the steam or the atomized water from the water feeding system, for setting and maintaining operating conditions such as duration of treatment, and for controlling and maintaining the preset condition;

said heating system comprising a pipe-like high temperature preheater, a pipe-like high temperature heater, a pipe-like super-high temperature heater, and a discharge pipe connected one after another, said pipe-like high temperature preheater being connected with a feeding pipe of the water feeding system at an introducing port provided at one end and used for generating the superheated steam by heating steam or atomized water introduced through the introducing port by applying voltage, said pipe-like high temperature heater being operable to turn the the superheated steam generated at the high temperature preheater to a steam of higher temperature by applying voltage, said super-high temperature heater being operable to turn the superheated steam heated at the high temperature heater to the steam of a still higher temperature by applying voltage, and said discharge pipe being operable to discharge the superheated steam generated at the super-high temperature heater into the treatment chamber.

* * * * *